United States Patent
Ross et al.

(10) Patent No.: US 9,351,755 B2
(45) Date of Patent: *May 31, 2016

(54) ULTRASONIC SURGICAL INSTRUMENTS

(71) Applicant: COVIDIEN LP, Mansfield, MA (US)

(72) Inventors: Anthony B. Ross, Boulder, CO (US); Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Arlen K. Ward, Thornton, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/599,645

(22) Filed: Jan. 19, 2015

(65) Prior Publication Data

US 2015/0133980 A1    May 14, 2015

Related U.S. Application Data

(63) Continuation of application No. 13/435,765, filed on Mar. 30, 2012, now Pat. No. 8,974,479.

(60) Provisional application No. 61/469,557, filed on Mar. 30, 2011.

(51) Int. Cl.
*A61B 17/00* (2006.01)
*A61B 17/32* (2006.01)
*A61B 17/29* (2006.01)

(52) U.S. Cl.
CPC .......... *A61B 17/320092* (2013.01); *A61B 2017/00026* (2013.01); *A61B 2017/2926* (2013.01)

(58) Field of Classification Search
CPC ............. A61B 17/320092; A61B 2017/00026; A61B 2017/2926; A61B 17/295
USPC ........... 606/169–174, 51, 52, 205–209, 1, 41, 606/45, 49
See application file for complete search history.

(56) References Cited

U.S. PATENT DOCUMENTS 4,522,206 A    6/1985    Whipple et al.
4,545,374 A    10/1985   Jacobson
(Continued)

FOREIGN PATENT DOCUMENTS

EP    01256323 A2    11/2002
JP    2000237204 A    9/2000
(Continued)

*Primary Examiner* — Katrina Stransky

(57) ABSTRACT

An ultrasonic surgical instrument is provided. The ultrasonic surgical instrument includes a housing having an elongated shaft extending therefrom. A first jaw member disposed at a distal end of the shaft is movable between open and clamping configurations. A pair of second jaw members disposed at the distal end of the shaft are movable between open and clamping configurations. A cutting blade extending to the distal end of the shaft is operably coupled to the housing. The pair of second jaw members and first jaw member are moveable to the clamping configuration to compress tissue of interest for removing moisture therefrom prior to the tissue of interest being treated.

19 Claims, 2 Drawing Sheets

(56) References Cited

U.S. PATENT DOCUMENTS

| | | |
|---|---|---|
| 5,330,471 A | 7/1994 | Eggers |
| 5,352,223 A | 10/1994 | McBrayer et al. |
| 5,395,369 A | 3/1995 | McBrayer et al. |
| 5,403,312 A | 4/1995 | Yates et al. |
| 5,432,689 A | 7/1995 | Sharrah et al. |
| 5,486,432 A | 1/1996 | Sharrah et al. |
| 5,496,317 A | 3/1996 | Goble et al. |
| 5,499,992 A | 3/1996 | Meade et al. |
| 5,549,606 A | 8/1996 | McBrayer et al. |
| 5,558,671 A | 9/1996 | Yates |
| 5,817,093 A | 10/1998 | Williamson, IV et al. |
| 5,833,690 A | 11/1998 | Yates et al. |
| 6,010,516 A | 1/2000 | Hulka |
| 6,063,098 A | 5/2000 | Houser et al. |
| 6,096,037 A | 8/2000 | Mulier et al. |
| 6,113,598 A | 9/2000 | Baker |
| 6,126,658 A | 10/2000 | Baker |
| 6,203,541 B1 | 3/2001 | Keppel |
| 6,228,080 B1 | 5/2001 | Gines |
| 6,358,268 B1 | 3/2002 | Hunt et al. |
| 6,398,779 B1 | 6/2002 | Buysse et al. |
| 6,443,952 B1 | 9/2002 | Mulier et al. |
| 6,443,953 B1 | 9/2002 | Perra et al. |
| 6,626,901 B1 | 9/2003 | Treat et al. |
| 6,682,527 B2 | 1/2004 | Strul |
| 6,719,755 B2 | 4/2004 | Sliwa, Jr. et al. |
| 6,773,409 B2 | 8/2004 | Truckai et al. |
| 6,773,434 B2 | 8/2004 | Ciarrocca |
| 6,776,780 B2 | 8/2004 | Mulier et al. |
| 6,786,905 B2 | 9/2004 | Swanson et al. |
| 6,796,981 B2 | 9/2004 | Wham et al. |
| 6,843,789 B2 | 1/2005 | Goble |
| 6,860,880 B2 | 3/2005 | Treat et al. |
| 6,893,434 B2 | 5/2005 | Fenton et al. |
| 6,893,435 B2 | 5/2005 | Goble |
| 7,101,372 B2 | 9/2006 | Dycus et al. |
| 7,101,373 B2 | 9/2006 | Dycus et al. |
| 7,118,587 B2 | 10/2006 | Dycus et al. |
| 7,131,971 B2 | 11/2006 | Dycus et al. |
| 7,147,637 B2 | 12/2006 | Goble |
| 7,229,456 B2 | 6/2007 | Lang et al. |
| 7,267,677 B2 | 9/2007 | Johnson et al. |
| 7,303,557 B2 | 12/2007 | Wham et al. |
| 7,364,577 B2 | 4/2008 | Wham et al. |
| 7,384,420 B2 | 6/2008 | Dycus et al. |
| 7,572,257 B2 | 8/2009 | Whayne et al. |
| 8,444,664 B2 | 5/2013 | Balanev et al. |
| 8,662,745 B2 | 3/2014 | Misuchenko et al. |
| 8,974,479 B2 | 3/2015 | Ross et al. |
| 2002/0103496 A1 | 8/2002 | Harper et al. |
| 2003/0069571 A1 | 4/2003 | Treat et al. |
| 2003/0212391 A1 | 11/2003 | Fenton et al. |
| 2004/0054364 A1 | 3/2004 | Aranyi et al. |
| 2004/0064151 A1 | 4/2004 | Mollenauer |
| 2004/0082952 A1 | 4/2004 | Dycus et al. |
| 2004/0116924 A1 | 6/2004 | Dycus et al. |
| 2004/0243125 A1 | 12/2004 | Dycus et al. |
| 2006/0189981 A1 | 8/2006 | Dycus et al. |
| 2007/0179499 A1 | 8/2007 | Garrison |
| 2008/0147106 A1 | 6/2008 | Mohr et al. |
| 2008/0312652 A1 | 12/2008 | Bell et al. |
| 2009/0069806 A1 | 3/2009 | De La Mora Levy et al. |
| 2009/0069842 A1 | 3/2009 | Lee et al. |
| 2009/0099582 A1 | 4/2009 | Isaacs et al. |
| 2009/0143796 A1 | 6/2009 | Stulen et al. |
| 2009/0157071 A1 | 6/2009 | Wham et al. |
| 2009/0157075 A1 | 6/2009 | Wham et al. |
| 2009/0198272 A1 | 8/2009 | Kerver et al. |
| 2010/0185197 A1 | 7/2010 | Sakao et al. |
| 2010/0198241 A1 | 8/2010 | Gerrah et al. |
| 2011/0190765 A1 | 8/2011 | Chojin |
| 2011/0241786 A1 | 10/2011 | Gilbert |
| 2012/0310229 A1 | 12/2012 | Gregg |
| 2013/0030328 A1 | 1/2013 | Dycus et al. |
| 2013/0085419 A1 | 4/2013 | Stoddard et al. |
| 2013/0197511 A1 | 8/2013 | Balanev et al. |

FOREIGN PATENT DOCUMENTS

| | | |
|---|---|---|
| WO | 9952489 | 10/1999 |
| WO | 03095028 A1 | 11/2003 |

ULTRASONIC SURGICAL INSTRUMENTS

CROSS-REFERENCE TO RELATED APPLICATIONS

This application is a continuation application of U.S. patent application Ser. No. 13/435,765, filed on Mar. 30, 2012, which claims the benefit of and priority to U.S. Provisional Patent Application No. 61/469,557, filed on Mar. 30, 2011, the entire contents of each of which is incorporated herein by reference.

BACKGROUND

1. Technical Field

The present disclosure relates to ultrasonic surgical instruments. More particularly, the present disclosure relates to ultrasonic surgical instruments including jaw members configured to compress tissue of interest for removing moisture therefrom prior to the tissue of interest being ultrasonically treated.

2. Description of Related Art

Ultrasonic energy-powered instruments configured to cut and/or fragment tissue are known in the art. Ultrasonic instruments, typically, include a transducer that is coupled to a probe/waveguide having an active member (e.g., cutting blade, shear, hook, ball, etc.) at a distal end thereof. In use, ultrasonic energy is utilized to vibrate (e.g., at frequency usually in the range of 20 KHz to 60 KHz) the active member to treat tissue of interest.

Ultrasonic instruments may include any of a variety of probe configurations to achieve a specific surgical result. For example, the probe configuration may include an active member in the form of a cutting blade that is combined with a movable jaw configured to grasp and/or manipulate tissue. Such ultrasonic instruments are suitable for use with a variety of medical procedures including open surgical procedures, luminal procedures, and endoscopic procedures.

During use of ultrasonic instruments, however, much of the energy that would otherwise be utilized to dissect or seal tissue with ultrasonic instruments is absorbed by the water present in tissue. When the water absorbs enough energy it either evaporates or is displaced to surrounding tissues, which, in turn, diminishes the intended surgical effect and tends to increase operative times. As can be appreciated, increased operative times may increase dissipation of heat beyond tissue of interest to adjacent tissue, e.g., thermal spread, which, in turn, may result in heat damage to adjacent tissue.

SUMMARY

In view of the foregoing, ultrasonic surgical instruments including jaw members configured to compress tissue of interest for removing moisture therefrom prior to the tissue of interest being ultrasonically treated may prove useful in the medical art.

Embodiments of the present disclosure are described in detail with reference to the drawing figures wherein like reference numerals identify similar or identical elements. As used herein, the term "distal" refers to a portion that is being described which is further from a user, while the term "proximal" refers to a portion that is being described which is closer to a user.

An aspect of the present disclosure provides an ultrasonic surgical instrument. The ultrasonic instrument includes a housing having an elongated shaft extending therefrom. A first jaw member is disposed at a distal end of the shaft and movable between an open configuration and a clamping configuration. A pair of second jaw members is disposed at the distal end of the shaft and movable between an open configuration and clamping configuration. A cutting blade extends to distal end of the shaft and operably couples to the housing. The cutting blade may be movable along a longitudinal axis defined through the shaft from a retracted configuration within the shaft to an extended configuration outside the shaft.

The second jaw members and first jaw member are moveable to the clamping configuration to compress tissue of interest for removing moisture therefrom prior to the tissue of interest being treated.

A lever may be operably coupled to the housing and moveable through a clamping stroke to move the first jaw member and second jaw members to the clamping configuration. The lever may be movable through a release stroke to move the second jaw members and the first jaw member from the clamping configuration to the open configuration.

At least one of the second jaw members may include an elongated slot defined in a tissue contacting surface thereof. The first jaw member may include a corresponding elongated slot defined in a tissue contacting surface thereof. The slots may be in vertical registration with one another and configured to receive the cutting blade therein when the first jaw member and second jaw members are in the clamping configuration.

At least one of the pair of second jaw members may include a generally arcuate configuration configured to receive the first jaw member therein when the first jaw member and second jaw members are in the clamping configuration. At least one of the second jaw members may include at least one sensor disposed thereon configured to detect moisture content of tissue of interest. The sensor(s) may communicate the detected moisture content of tissue of interest to at least one controller operably associated with a generator of the ultrasonic surgical instrument. The at least one controller may be configured to determine the moisture content and provide an indication to a user that the tissue of interest is ready to be treated.

An aspect of the present disclosure provides an ultrasonic surgical instrument. The ultrasonic instrument includes a housing having an elongated shaft extending therefrom and defining a longitudinal axis therethrough. The first jaw member is disposed at a distal end of the shaft and movable between an open configuration and clamping configuration. A pair of second jaw members disposed at the distal end of the shaft is movable between an open configuration and clamping configuration. At least one of the second jaw members is configured to receive the first jaw member therein when the first jaw member and second jaw members are in the clamping configuration. A cutting blade extends to the distal end of the shaft and operably couples to the housing. The cutting blade is movable along the longitudinal axis from a retracted configuration to an extended configuration. The second jaw members and first jaw member are movable to the clamping configuration to compress tissue of interest for removing moisture therefrom prior to the tissue of interest being treated.

A lever may be operably coupled to the housing and moveable through a clamping stroke to move the first jaw member and second jaw members to the clamping configuration. The lever may be movable through a release stroke to move the second jaw members and the first jaw member from the clamping configuration to the open configuration.

At least one of the second jaw members may include an elongated slot defined in a tissue contacting surface thereof.

Moreover, the first jaw member may include a corresponding elongated slot defined in a tissue contacting surface thereof. The slots may be in vertical registration with one another and configured to receive the cutting blade therein when the first jaw member and pair of second jaw members are in the clamping configuration and the cutting blade is in the extended configuration.

The at least one second jaw member configured to receive the first jaw member therein may include a generally arcuate configuration. At least one of the second jaw members may include at least one sensor disposed thereon configured to detect moisture content of tissue of interest. The at least sensor may communicate the detected moisture content of tissue of interest to at least one controller operably associated with a generator of the ultrasonic surgical instrument. The at least one controller may be configured to receive the detected moisture content of tissue communicated by the sensor, to determine the moisture content of tissue of interest therefrom, and provide an indication to a user that the tissue of interest is ready to be treated.

An aspect of the present disclosure provides a method for ultrasonically treating tissue of interest. Tissue of interest is positioned between a pair of second jaw members of an ultrasonic instrument. The pair of second jaw members are approximated toward one another to compress the tissue of interest. Approximation of the second jaw members toward one another moves a first jaw member towards at least one of the second jaw members. The cutting blade is activated to treat the compressed tissue of interest.

At least one of the second jaw members may be provided with at least one sensor disposed thereon configured to detect moisture content of the tissue of interest. The detected moisture content of tissue of interest may be communicated to at least one controller operably associated with a generator of the ultrasonic surgical instrument. The moisture content of tissue of interest compressed between the first jaw member and second pair of jaw member may be determined and an indication may be provided to a user that the tissue of interest is ready to be treated. Prior to approximating the first jaw member and cutting blade towards one another, the cutting blade may be actuated to move from a retracted configuration to an extended configuration.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
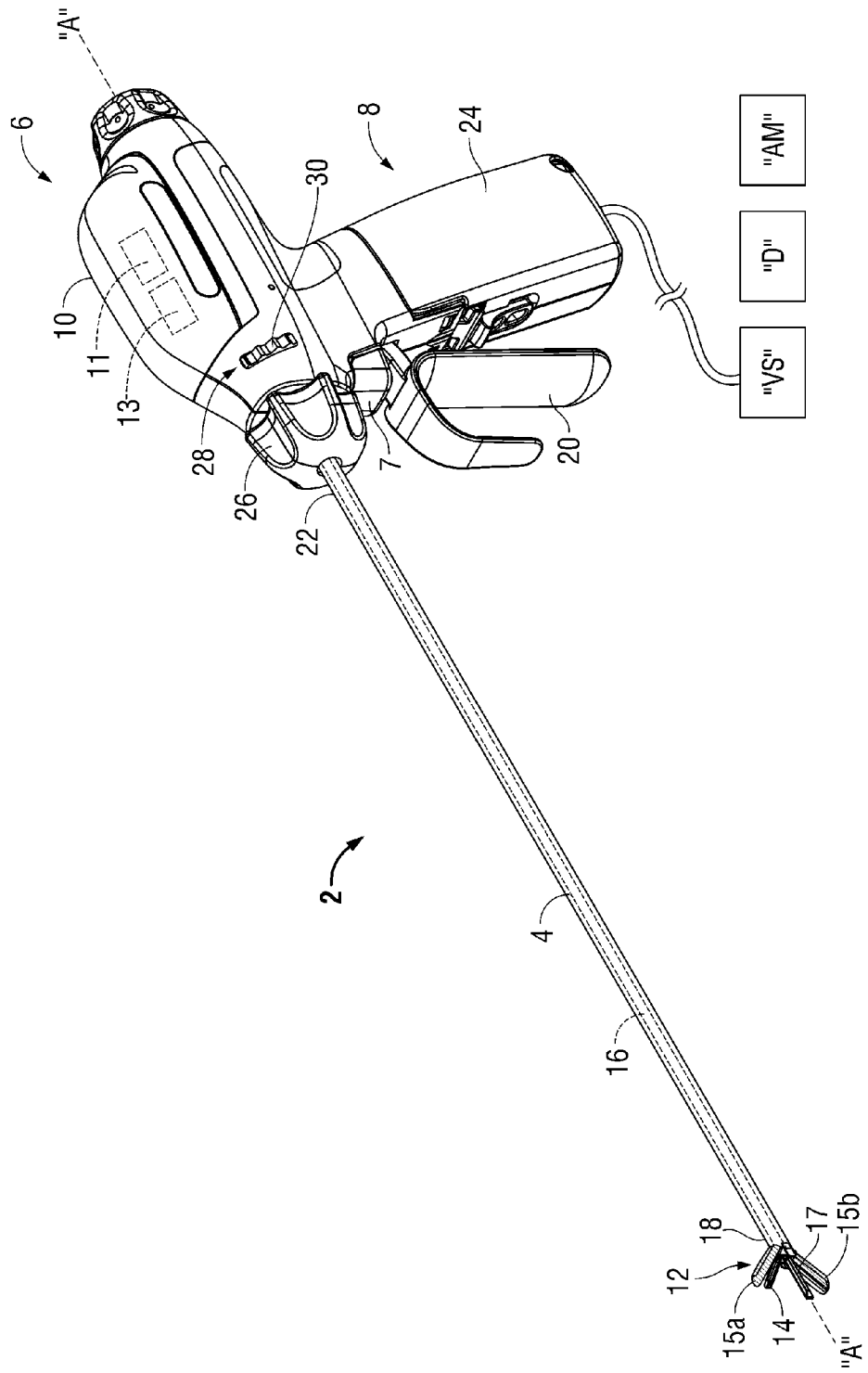
FIG. 1 is a right, perspective view of an ultrasonic instrument according to an embodiment of the present disclosure.

Turning now to FIG. 1, an ultrasonic surgical instrument 2 (instrument 2) according to an embodiment of the present disclosure is illustrated. In the illustrated embodiments, instrument 2 is described herein as being battery powered. Alternatively, instrument 2 may be externally powered, e.g., via a remote ultrasonic generator that couples to the instrument 2.

Briefly, instrument 2 includes a housing 6 configured to house one or more components, e.g., transducer (not explicitly shown), a probe 16, and electrical circuitry that is configured for electrical communication with a battery assembly 8 of instrument 2. A proximal end of housing 6 is configured to releasably couple to an ultrasonic generator 10 and battery assembly 8. A distal end of the housing 6 is configured to support and/or couple to a proximal end 22 of a shaft 4 having a longitudinal axis "A-A" defined therethrough. A rotation knob 26 operably couples to housing 6 and is configured to rotate shaft 4 approximately 360° in either direction about the longitudinal axis "A-A." Generator 10 includes the transducer that is coupled to probe 16 via a torque adapter (not explicitly shown) and configured to produce vibratory motion of a cutting blade 17 disposed at a distal end of probe 16 when a trigger 7 is depressed. This vibratory motion of cutting blade 17 is utilized to treat tissue of interest. Battery assembly 8 includes a handpiece 24 having a battery (not explicitly shown) operably disposed therein.

With reference to FIGS. 1-4, an end effector 12 includes first jaw member 14 that is supported at a distal end 18 of the shaft 4 adjacent cutting blade 17. Jaw member 14 is pivotably supported at the distal end of the shaft 4 via a pivot pin 3 (FIG. 2) and functions as a clamping jaw. In particular, jaw member 14 is movable relative to cutting blade 17 (and/or the distal end 18 of the shaft 4) between an open configuration (FIGS. 1 and 2) and a clamping configuration (FIGS. 3 and 4) to clamp tissue when a lever or movable handle 20 (FIG. 1) is actuated. Jaw member 14 and cutting blade 17 are configured to collectively grasp and ultrasonically treat tissue. In particular, when tissue is positioned between jaw member 14 and cutting blade 17, the cutting blade is configured to vibrate at a specific frequency (e.g., at frequency in the range from about 20 KHz to about 60 KHz) to treat tissue.

Figure 4:
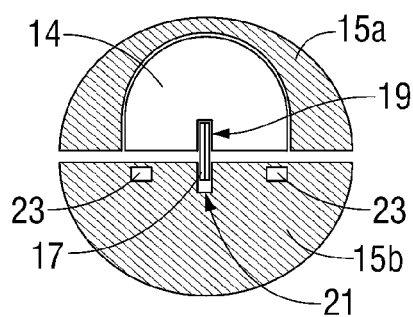
FIG. 4 is an enlarged, cross-sectional view taken along line segment "4-4" in FIG. 3.

End effector 12 includes a pair of second jaw members 15a, that are independently movable to a clamping configuration to grasp tissue, as best seen in FIGS. 1 and 4. To this end, jaw member 14 is shaped to compliment a shape of second jaw member 15a to facilitate receipt of jaw member 14 within the second jaw member 15a when second jaw members 15a, 15b are approximated toward one another to grasp tissueb.

Figure 2:
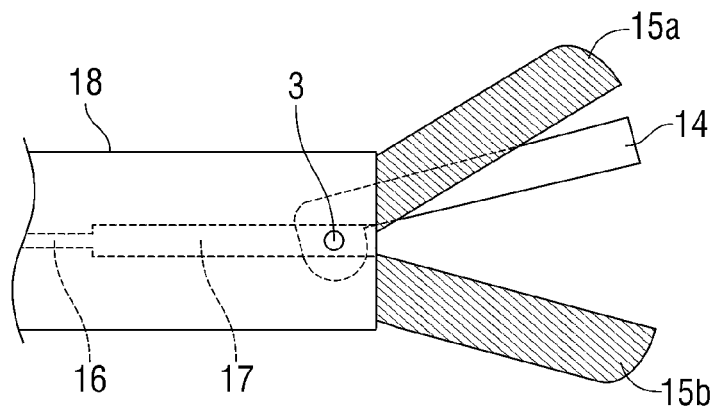
FIG. 2 is an enlarged, side, schematic view of a distal end of the ultrasonic instrument depicted in FIG. 1 with a cutting blade illustrated in a retracted configuration.
Figure 3:
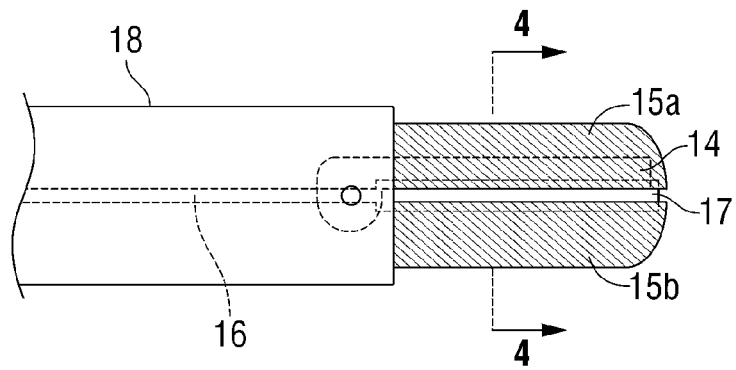
FIG. 3 is an enlarged, side, schematic view of the distal end depicted in FIG. 2 with jaw members illustrated in a clamping configuration.

One or more elongated slots 19 are provided on jaw member 14 and configured to receive cutting blade 17 therethrough when cutting blade 17 is moved from a retracted configuration (FIG. 2) to an extended configuration (FIGS. 1, 3 and 4).

Continuing with reference to FIGS. 2-4, second jaw members 15a, 15b are movable from an open configuration (FIGS. 1 and 2) to a clamping configuration (FIGS. 3 and 4) when the movable handle 20 is moved proximally. In the illustrated embodiments, second jaw members 15a, 15b may be coupled to the shaft 4 via the pivot pin 3, In the clamping configuration, jaw members 15a and 15b are configured to compress tissue of interest to remove moisture therefrom (e.g., desiccate) prior to the tissue of interest being treated, i.e., desiccate tissue of interest. By desiccating the tissue of interest, less ultrasonic energy is required, which, in turn, decreases the amount of operative time of instrument 2, which, in turn, may decrease the likelihood of "thermal spread" from occurring.

Second jaw members 15a, 15b may be made from any suitable material including, but not limited to metal, plastic, ceramic, etc. In the illustrated embodiment, second jaw members 15a, 15b are made from ceramic. The hardness of the ceramic facilitates compressing tissue of interest positioned between second jaw members 15a (including jaw member 14), 15b.

In the illustrated embodiment, second jaw member 15a is configured to receive jaw member 14 therein when the second jaw members 15a, 15b are moved to the clamping configuration. To this end, second jaw member 15a includes a generally arcuate configuration that compliments the configuration of the jaw member 14, as best seen in FIG. 4.

One or more elongated slots 21 are provided on second jaw member 15b and configured to receive cutting blade 17 therethrough when cutting blade 17 is moved from the retracted configuration (FIG. 2) to the extended configuration (FIGS. 1, 3 and 4). In some embodiments, cutting blade 17 may be moved to the extended configuration prior to the second members 15a, 15b being moved to the clamping configuration. In some embodiments, cutting blade 17 may be moved to the extended configuration subsequent to the second members 15a, 15b being moved to the clamping configuration. The particular positioning sequence of cutting blade 17 with respect to second jaw members 15a, 15b may depend on a specific surgical procedure, a specific type of tissue to be treated, a surgeon's preference, and so forth.

One or more sensors 23 (FIG. 4) may be positioned on one or both of the second jaw members 15a, 15b. In the illustrated embodiment, for example, a pair of sensors 23 is positioned on the second jaw member 15b and is configured to detect a moisture content of tissue of interest, e.g., tissue of interest positioned adjacent sensors 23. With this purpose in mind, sensors 23 may be any suitable type of sensors including, but not limited to smart sensors, fiber optic sensors and the like. Sensors 23 may be configured to analyze one of more properties of tissue of interest to determine moisture content thereof. For example, scattering and absorption properties of tissue of interest may be utilized to determine moisture content of tissue of interest.

Sensors 23 may be configured to communicate with one or more modules of the generator 10 and/or the battery assembly 8. In one particular embodiment, for example, sensor 23 may be configured to provide data pertaining to moisture content of tissue of interest to a controller 11 (FIG. 1) of the generator 10 and/or battery assembly 8. In the illustrated embodiments, controller 10 is provided with the generator 10 (FIG. 1). Controller 11 may analyze the data pertaining to moisture content of tissue of interest and utilize one or more control algorithms to facilitate a user in determining when tissue of interest is sufficiently desiccated. In one particular embodiment, for example, instrument 2 and controller 11 may be configured to provide one or more indications, e.g., an audio indication "A", a visual indication "V", etc., to a user indicating that tissue of interest is sufficiently desiccated.

Alternatively, controller 11 may be configured to communicate with one or more pressure controllers 13 (FIG. 1) configured to automatically control an amount of compression provided by the second jaw members 15a, 15b to tissue of interest positioned therebetween. In this particular embodiment, one or more drive rods, servos, links, gears and the like may be provided with the instrument 2 to provide mechanical and/or electrical communication between the pressure controller(s) 13 and jaw members 15a and 15b to adjust a compressive force applied to tissue of interest. In one particular embodiment, for example, pressure controller 13 may function as a "micro-tuner" configured to adjust the amount of compression after the second jaw members 15a, 15b are moved to clamping configuration. In this instance, controller 11 determines a moisture content of tissue of interest compressed between the second jaw members 15a, 15b. If controller 11 determines that more moisture needs to be removed from tissue of interest, controller 11 sends a command signal to pressure controller 13 to further compress second jaw members 15a, 15b to remove more moisture, e.g., further desiccate tissue.

Referring again to FIG. 1, a switching mechanism 28 may be disposed on the housing 6 and operably couple to cutting blade 17 to move cutting blade 17 from the retracted configuration (shown in phantom in FIG. 2) to the extended configuration (FIGS. 1, 3 and 4). Switching mechanism 28 may be any suitable type of switching mechanism including but not limited to push-buttons, dials, slides, etc. In accordance with one particular embodiment, switching mechanism 28 includes a dial 30 positioned at a distal end of the housing 6. Dial 30 operably couples to the probe 16 and is configured to move cutting blade 17 to the extended configuration when the dial 30 is moved in a counter-clockwise direction and is configured to move the cutting blade 17 back to the retracted configuration when the dial 30 is moved in a clockwise direction. One or more components, such as, for example, drive rods, servos, links, gears and the like may be provided with the instrument 2 to provide mechanical and/or electrical communication between the dial 30 and probe 16.

While switching mechanism 28 has been provided herein to actuate cutting blade 17, it is within the purview of the present disclosure that cutting blade 17 be operational without the switching mechanism 28. For example, when cutting blade 17 is not configured to retract, and is supported outside shaft 4 and adjacent jaw member 14.

In the illustrated embodiment, lever 20 is operably coupled to housing 6 and is configured to actuate jaw member 14 and second jaw members 15a, 15b from the open configuration to the clamping configuration. Specifically, lever 20 is movable through a clamping stroke to move first jaw member 14 and second jaw members 15a, 15b to the clamping configuration (FIGS. 3 and 4). A latching mechanism (not shown) may be provided on the lever 20 to latch the lever 20 in a predetermined configuration that correlates to jaw members 14, and 15a, 15b being in one or more clamping configurations. Lever 20 is also movable through a release stroke configured to release the lever 20 from the latched configuration and to move first jaw member 14 and second jaw members 15a, 15b back to the open configuration (FIGS. 1 and 2).

In operation of one particular embodiment of the instrument 2, and with cutting blade in the extended configuration, tissue may be positioned between jaw member 14 and second jaw members 15a, 15b. Subsequently, lever 20 may be moved through the clamping stroke to move second jaws 15a, 15b from the open configuration to the clamping configuration. In the illustrated embodiment, movement of the second jaw member 15a to the clamping configuration moves jaw member 14 to the clamping configuration. In this embodiment, if a user releases lever 20, lever 20 moves back to its original configuration and second jaw members 15a, 15b move back to the open configuration. In some embodiments, however, the latch may be utilized to latch lever 20 is one or more predetermined configurations that correlate to a specific clamping configuration of second jaw members 15a, 15b. In this embodiment, the latch maintains second jaw members 15a, 15b in a specific clamping configuration regardless of lever 20 being released.

With tissue clamped between second jaw member 15a (including jaw member 14 seated therein) and second jaw member 15b, sensors 23 detect moisture content of the compressed tissue of interest. Sensors 23 communicates this detected moisture content to moisture control module 11 to determine the moisture content of the compressed tissue of interest compressed. If moisture control module 11 determines that the compressed tissue of interest is sufficiently desiccated, an indication, e.g., an audio indication "A" and/or a visual indication "V," is provided to a user indicating that tissue of interest is ready to be treated. If, however, moisture control module 11 determines that the compressed tissue of interest is not sufficiently desiccated an indication, e.g., an audio indication "A" and/or a visual indication "V," is provided to a user indicating that further compression of the second jaw members 15a, 15b is required. As noted above, in the latter instance, pressure controller 13 may be utilized to automatically control the compressive force provided by second jaw members 15a, 15b to tissue of interest positioned therebetween.

Subsequent to tissue of interest being sufficiently desiccated, and with second jaw members 15a, 15b in the clamping configuration, trigger 7 may be activated to actuate cutting blade 17 to treat tissue of interest.

The unique configuration of the instrument 2 including second jaw members 15a, 15b minimizes the operative time of instrument 2 required to effectively treat tissue of interest and overcomes the aforementioned drawbacks that are typically associated with conventional ultrasonic instruments. That is, the likelihood of heat damage occurring to tissue adjacent tissue of interest that has been ultrasonically treated by cutting blade 17 is reduced, if not eliminated.

From the foregoing and with reference to the various figure drawings, those skilled in the art will appreciate that certain modifications can also be made to the present disclosure without departing from the scope of the same. For example, one or more desiccants "D" may be utilized to dry tissue of interest prior to treatment thereof (FIG. 1). Suitable desiccants "D" may include, but are not limited to silica gel, activated charcoal, calcium sulfate, calcium chloride, montmorillonite clay, and molecular sieves. In one particular embodiment, one or more of the aforementioned desiccants may be applied to the tissue of interest to facilitate drying the tissue of interest prior to compressing the tissue with second jaw members 15a, 15b.

Moreover, it may prove advantageous to utilize one or more absorbent materials "AM" to dry tissue of interest prior to treatment thereof (FIG. 1). Absorbent materials "AM" may include, but are not limited to cotton swabs, meshes, sponges and the like. In one particular embodiment, one or more of the aforementioned absorbent materials "AB" may be utilized to wipe the tissue of interest to facilitate drying the tissue of interest prior to compressing the tissue with second jaw members 15a, 15b.

Further, it may prove advantageous to utilize one or more vacuum sources "VS" to dry tissue of interest prior to treatment thereof (FIG. 1). In embodiments, the vacuum source "VS" may be a component of the instrument 2 or may be a component separate from the instrument 2. In one particular embodiment, vacuum source "VS" may be utilized to abstract moisture from the tissue of interest to facilitate drying the tissue of interest prior to compressing the tissue with second jaw members 15a, 15b.

In some embodiments, it may prove advantageous to move second jaw members 15a, 15b back to the open configuration prior to actuating cutting blade 17 to treat tissue. In this instance, lever 20 may be operable in a two-stroke release sequence. More particularly, lever 20 may be movable through a first release stroke to move second jaw members 15a, 15b from the clamping configuration to the open configuration and movable through a second stroke to move the jaw member 14 from the clamping configuration to the open configuration.

In some embodiments, jaw member 14 may be configured to translate along the longitudinal axis from a retracted configuration to an extended configuration. This embodiment is particularly useful when jaw member 14 is configured to move from the open configuration to the closed configuration independent of second jaw member 15a. As can be appreciated, certain modifications may be made to instrument 2 and operative components associated therewith, e.g., lever 20, controller 11, pressure controller 13 and/or cutting blade 17, when jaw member 14 is configured to retract. For example, it may prove advantageous to provide second jaw member 15a without the generally arcuate configuration, i.e., configure second jaw member 15a similarly to second jaw member 15b. Moreover, a second lever (not shown) may be utilized and configured to move jaw member 14 along the longitudinal axis and about pivot pin 3.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
a housing having an elongated shaft extending therefrom;
first, second, and third jaw members disposed at a distal end of the shaft, the first jaw member movable relative to the shaft and each of the second and third jaw members between a first position and a second position, the second and third jaw members movable relative to one another between an open configuration and a clamping configuration, wherein when the first jaw member is in the second position and the second and third jaw members are in the clamping configuration, the first jaw member is nested within the second jaw member.

2. The ultrasonic surgical instrument according to claim 1, wherein a lever is operably coupled to the housing and is moveable through a clamping stroke to move the first jaw member from the first position to the second position and the second and third jaw members from the open configuration to the clamping configuration, the lever further movable through a release stroke to move the first jaw member from the second position to the first position and the second and third jaw members from the clamping configuration to the open configuration.

3. The ultrasonic surgical instrument according to claim 1, wherein the third jaw member includes an elongated slot defined in a tissue contacting surface thereof and the first jaw member includes a corresponding elongated slot defined in a tissue contacting surface thereof, the slots in vertical registration with one another and configured to receive a cutting blade therein when the first jaw member is in the second position and the second and third jaw members are in the clamping configuration.

4. The ultrasonic surgical instrument according to claim 1, wherein the second jaw member includes a generally arcuate configuration and the first jaw member includes a complementary configuration to facilitate nesting of the first jaw member within the second jaw member.

5. The ultrasonic surgical instrument according to claim 1, wherein at least one of the second or third jaw members includes at least one sensor disposed thereon configured to detect moisture content of tissue of interest.

6. The ultrasonic surgical instrument according to claim 5, wherein the at least one sensor communicates a detected moisture content of tissue of interest to a controller operably associated with the ultrasonic surgical instrument.

7. The ultrasonic surgical instrument according to claim 6, wherein the controller is configured to provide an indication to a user that the tissue of interest is ready to be treated.

8. The ultrasonic surgical instrument according to claim 1, wherein a cutting blade is movable along a longitudinal axis defined through the shaft from a retracted configuration positioned within the shaft to an extended configuration position outside the shaft.

9. An ultrasonic surgical instrument, comprising:
  an end effector having first, second, and third jaw members pivotally movable relative to one another, the first jaw member movable relative to each of the second and third jaw members between a first position and a second position, the second and third jaw members movable relative to each other between an open configuration and a clamping configuration, wherein when the second and third jaw members are in the clamping configuration, the first jaw member is nested within the second jaw member.

10. The ultrasonic surgical instrument according to claim 9, wherein the third jaw member includes an elongated slot defined in a tissue contacting surface thereof and the first jaw member includes a corresponding elongated slot defined in a tissue contacting surface thereof, the slots in vertical registration with one another and configured to receive a cutting blade therein when the first jaw member is in the second position and the second and third jaw members are in the clamping configuration.

11. The ultrasonic surgical instrument according to claim 9, wherein the second jaw member includes a generally arcuate configuration and the first jaw member includes a complementary configuration to facilitate nesting of the first jaw member within the second jaw member.

12. The ultrasonic surgical instrument according to claim 9, wherein at least one of the second or third jaw members includes at least one sensor disposed thereon configured to detect moisture content of tissue of interest.

13. The ultrasonic surgical instrument according to claim 12, wherein the at least one sensor communicates a detected moisture content of tissue of interest to a controller operably associated with the ultrasonic surgical instrument.

14. The ultrasonic surgical instrument according to claim 13, wherein the controller is configured to provide an indication to a user that the tissue of interest is ready to be treated.

15. A method for ultrasonically treating tissue of interest, comprising:
  positioning tissue of interest adjacent a first jaw member and between second and third jaw members of an ultrasonic instrument; and
  approximating the second and third jaw members toward one another to clamp the tissue of interest, wherein approximating the second and third jaw members toward one another moves the first jaw member relative to each of the second and third jaw members such that the first jaw member is nested within the second jaw member.

16. The method according to claim 15, further including activating a cutting blade to treat the clamped tissue of interest.

17. The method according to claim 16, further including detecting a moisture content of tissue of interest.

18. The method according to claim 17, further including:
  communicating the detected moisture content of tissue of interest; and
  providing an indication that the tissue of interest is ready to be treated.

19. The method according to claim 16, wherein prior to approximating the second and third jaw members, the cutting blade is actuated to move from a retracted configuration to an extended configuration.

* * * * *